United States Patent
Schnitzer (10) Patent No.: US 7,091,500 B2
(45) Date of Patent: Aug. 15, 2006

(54) MULTI-PHOTON ENDOSCOPIC IMAGING SYSTEM

(75) Inventor: Mark J Schnitzer, Hoboken, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 454 days.

(21) Appl. No.: 10/600,675

(22) Filed: Jun. 20, 2003

(65) Prior Publication Data

US 2004/0260148 A1    Dec. 23, 2004

(51) Int. Cl.
*G01N 21/64*    (2006.01)

(52) U.S. Cl. .................................. 250/458.1
(58) Field of Classification Search ............. 250/458.1
See application file for complete search history.

(56) References Cited

U.S. PATENT DOCUMENTS

| | | | |
|---|---|---|---|
| 3,655,259 A | 4/1972 | Miyauchi et al. ........... | 359/376 |
| 4,515,444 A | 5/1985 | Prescott et al. ............. | 350/413 |
| 4,723,843 A | 2/1988 | Zobel ......................... | 350/573 |
| 4,880,298 A | 11/1989 | Takada ........................ | 359/654 |
| 5,034,613 A | 7/1991 | Denk et al. .................. | 250/458 |
| 5,361,166 A | 11/1994 | Atkinson et al. ........... | 359/654 |
| 5,377,047 A | 12/1994 | Broome et al. ............. | 359/654 |
| 5,548,113 A | 8/1996 | Goldberg et al. ........... | 359/368 |
| 5,804,813 A | 9/1998 | Wang et al. ............. | 250/201.3 |
| 6,166,385 A | 12/2000 | Webb et al. ............. | 250/458.1 |
| 6,341,036 B1 | 1/2002 | Tearney et al. ............. | 359/368 |
| 6,795,199 B1 * | 9/2004 | Suhami ....................... | 356/601 |
| 2002/0080359 A1 * | 6/2002 | Denk et al. ................. | 356/446 |

FOREIGN PATENT DOCUMENTS

| | | |
|---|---|---|
| WO | WO 94/07142 | 3/1994 |
| WO | WO 98/38907 | 9/1998 |
| WO | WO 99/44089 | 9/1999 |
| WO | WO 01/59423 A2 | 8/2001 |
| WO | WO 02/48688 A1 | 6/2002 |

OTHER PUBLICATIONS

"Research Reduces Cost of Endoscopes," Optics and Laser Technology, Elsevier Science Publishers BV., Amsterdam, NL, vol. 25, No. 6, Dec. 1, 1993, p. 400.
U.S. Appl. No. 09/919,017, filed Jul. 31, 2001, Reed et al.
U.S. Appl. No. 10/082,870, filed Feb. 25, 2002, Schnitzer.
U.S. Appl. No. 10/029,576, filed Dec. 21, 2001, Schnitzer.

* cited by examiner

*Primary Examiner*—David Porta
*Assistant Examiner*—Mindy Vu
(74) *Attorney, Agent, or Firm*—John F. McCabe (57) ABSTRACT

An imaging system includes a pulsed laser, a pre-compensator for chromatic dispersion, a transmission optical fiber, and a GRIN lens. The pre-compensator chirps optical pulses received from the laser. The transmission optical fiber transports the chirped optical pulses from the pre-compensator. The GRIN lens receives the transported optical pulses from the transmission optical fiber. The GRIN lens has a wider optical core than the transmission optical fiber and substantially narrows the transported optical pulses received from the transmission optical fiber.

16 Claims, 8 Drawing Sheets

MULTI-PHOTON ENDOSCOPIC IMAGING SYSTEM

BACKGROUND

1. Field of the Invention

The invention relates generally to multi-photon imaging systems.

2. Discussion of the Related Art

In multi-photon imaging, molecules are excited via absorptions of two or more photons and imaged via light emitted during molecular de-excitations. The imaging light has a different wavelength than the exciting light and is emitted by selected molecular species, e.g., dye molecules. For these reasons, multi-photon imaging can produce tissue-selective images, e.g., of blood or neural tissue. In medical diagnostics, tissue-selective images are useful for in vivo analysis. Unfortunately, rates for multi-photon absorptions are low unless illumination has a high peak intensity. For example, rates for two-photon absorption events grow as a square of the illumination intensity.

For imaging applications, acceptable multi-photon absorption rates usually require intense illumination. Some imaging systems use very short optical pulses to produce the required intense illumination. One such imaging system is a scanning endoscopic microscope 10 illustrated in FIGS. 1 and 2.

Figure 1:
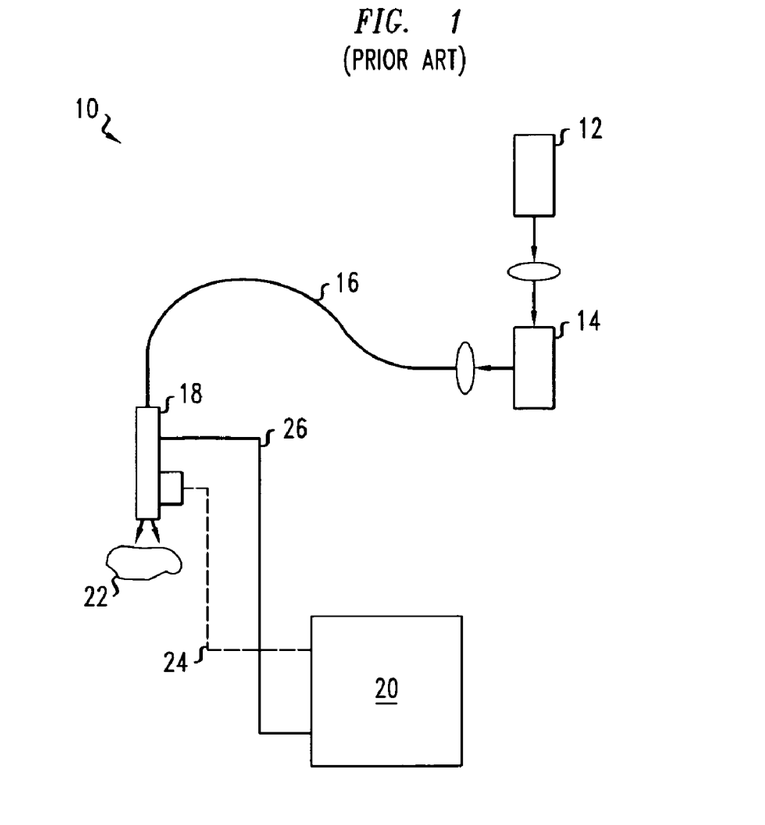
FIG. 1 illustrates a conventional endoscopic microscope for producing scanned multi-photon images of a sample.

Referring to FIG. 1, the scanning endoscopic microscope 10 includes a laser 12, a pre-compensator 14, a transmission optical fiber 16, a remote endoscopic probe 18, and a processor 20. The laser 12 emits short optical pulses with high peak intensities. The peak intensities are high enough to generate acceptable rates of molecular multi-photon absorptions in sample 22. The pre-compensator 14 chirps optical pulses to pre-compensate for the subsequent effects of the chromatic dispersion in the transmission optical fiber 16. The transmission optical fiber 16 delivers the optical pulses to the remote endoscopic probe 18. The remote endoscopic probe 18 scans the sample 22 with the optical pulses and measures intensities of light emitted by molecules that undergo absorptions of two or more photons during the scanning. The processor 20 constructs an image of the sample 22 from measured intensities received via line 24 and electrical data indicative received via line 26. The electrical data is indicative of scanning positions in the sample 22.

Figure 2:
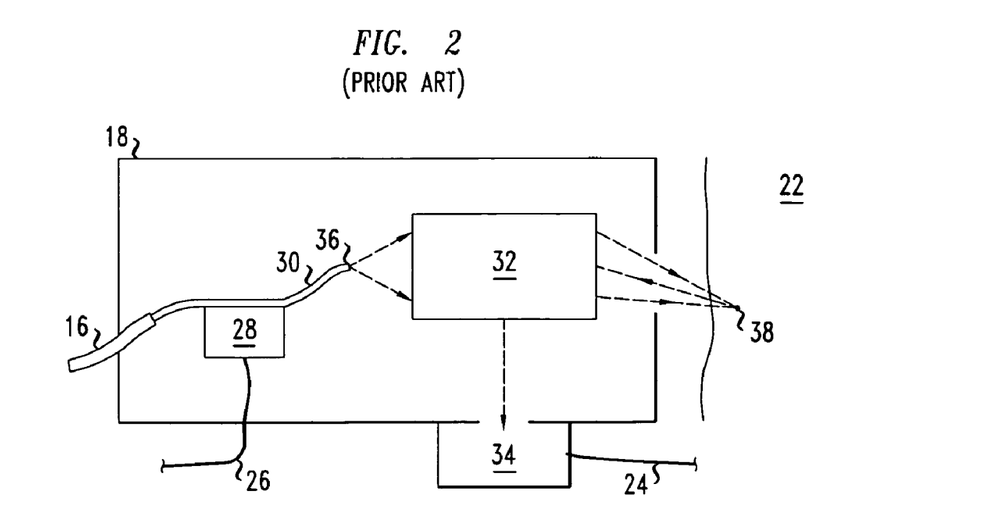
FIG. 2 illustrates a remote probe of the endoscopic microscope of FIG. 1.

Referring to FIG. 2, the probe 18 includes a mechanical oscillator 28, a segment of optical fiber 30, a lens system 32, and a light detector 34. The mechanical oscillator 28 drives the segment of optical fiber 30 so that the fiber end 36 performs an oscillatory 2-dimensional motion. The lens 32 focuses light emitted from the fiber end 36, i.e., optical pulses received from transmission fiber 16, to an illumination spot 38 in the sample 22. The illumination spot 38 makes a scanning motion in the sample 22 that corresponds to the oscillatory 2-dimensional motion of the fiber end 36. The light detector 34 measures intensities of light emitted in response to molecular multi-photon absorptions in the sample 22. The processor 22 uses the measured light intensities and electrical data indicative of the position of the fiber end 36 to construct a scanned image of the sample 22.

Molecular multi-photon absorptions have rates that are acceptably high for imaging if illumination optical pulses have high peak-intensities. Unfortunately, transmission through optical fibers often broadens optical pulses thereby lowering peak intensities. In ordinary optical fibers, both chromatic dispersion and nonlinear optical effects such as self-phase modulation can broaden optical pulses.

Referring to FIG. 1, to inhibit broadening by chromatic dispersion, pre-compensator 14 pre-chirps illumination optical pulses prior to their insertion into transmission optical fiber 16. The chirping places longer wavelength components behind shorter wavelength components in the optical pulses. During propagation through the transmission optical fiber 16, the longer wavelength components propagate faster than the shorter wavelength due to chromatic dispersion. The faster propagation of the longer wavelength components produces temporal narrowing of the pre-chirped optical pulses thereby counteracting the broadening effect chromatic dispersion would otherwise produce in the absence of chirping.

Referring to FIG. 1, to inhibit broadening of pre-chirped optical pulses by nonlinear optical effects, imaging system 10 maintains light intensities in transmission optical fiber 16 at low values. This reduces nonlinear optical interactions, because such interactions have low rates at low light intensities. The light intensities may be maintained at the low values by lowering initial peak intensities of the optical pulses produced by laser 12. The light intensities may also be maintained at low values by using a multi-mode fiber for transmission optical fiber 16. In the multi-mode fiber, light intensities are lower than in a single mode fiber (SMF) especially when a device inserts the optical pulses in a manner that causes the opiical pulses to laterally spread out thereby filling the larger core of multi-mode optical fiber. Unfortunately, a multi-modal fiber can also introduce pulse broadening due to modal dispersion.

It is desirable to have improved systems for producing multi-photon images in-vivo.

SUMMARY

In transmission optical fibers, nonlinear optical effects can temporally broaden pre-chirped optical pulses if the optical pulses have high peak intensities. Herein, multi-photon imaging systems have compound transmission pathways that avoid broadening from nonlinear optical effects in optical fiber by keeping peak intensities low therein. The illumination portions of the imaging systems include a pre-compensator for chromatic dispersion, a transmission optical fiber and a graded refractive index (GRIN) lens. The compound transmission pathway evolves temporal widths of optical pulses so that the pulses have low peak intensities along the entire pathway. For that reason, nonlinear optical effects do not substantially broaden the optical pulses. Furthermore, the transmission pathway avoids multi-modal dispersion and evolves optical pulses so that chromatic dispersion produces optical pulses with narrow temporal widths at the sample to be imaged. For these reasons, the optical pulses have high peak intensities in the sample as desirable for illumination light in multi-photon imaging.

In one aspect, the invention features an imaging system that includes a pulsed laser, a pre-compensator, a transmission optical fiber, and a GRIN lens with a wider optical core than the transmission optical fiber. The pre-compensator is configured to receive optical pulses produced by the pulsed laser and to chirp the optical pulses to pre-compensate for chromatic dispersion. The transmission optical fiber is configured to receive the chirped optical pulses from the pre-compensator. The GRIN lens is configured to receive the optical pulses transported by the transmission optical fiber and to substantially temporally narrow the optical pulses received from the transmission optical fiber.

In another aspect, the invention features a method for operating an imaging system. The method includes steps of chirping optical pulses, transmitting the chirped optical pulses through a transmission optical fiber wherein chromatic dispersion narrows the chirped optical pulses, and transmitting through a GRIN lens the optical pulses transmitted through the transmission optical fiber. The step of transmitting through a GRIN lens causes further substantial temporal narrowing of the optical pulses transmitted through the transmission optical fiber.

BRIEF DESCRIPTION OF THE DRAWINGS

In the Figures and text, similar reference numbers indicate elements with similar functions.

DETAILED DESCRIPTION OF ILLUSTRATIVE EMBODIMENTS

Figure 3:
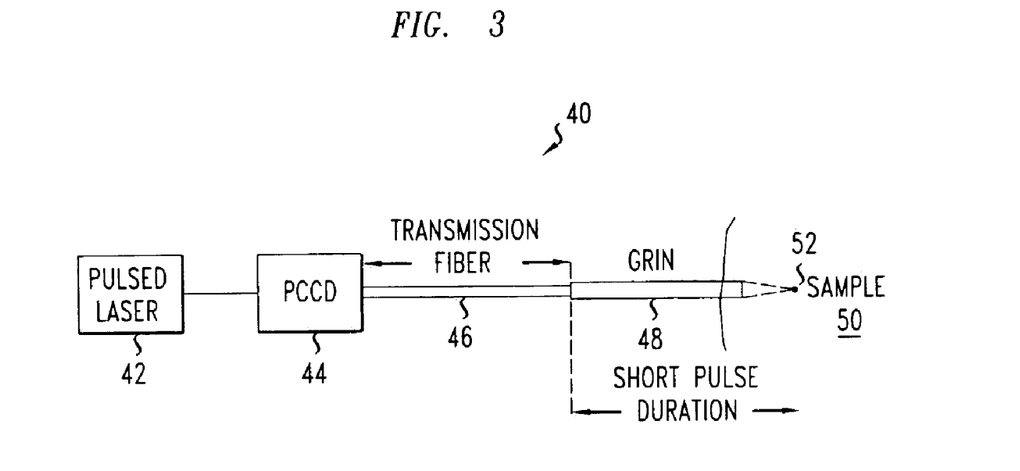
FIG. 3 illustrates the illumination portion of a scanning multi-photon imaging system having a remote endoscopic probe.

FIG. 3 schematically illustrates an illumination portion 40 of a scanning multi-photon imaging system. The illumination portion 40 includes a pulsed laser 42, a pre-compensator for chromatic dispersion (PCCD) 44, a transmission optical fiber 46, and a graded index (GRIN) lens 48. The pulsed laser 42 produces optical pulses with short temporal widths and high peak intensities. The high peak intensities are suitable for illumination light in multi-photon imaging. The PCCD 44 chirps the optical pulses from the laser 42 in a manner that pre-compensates for chromatic dispersion in both the transmission optical fiber 46 and the GRIN lens 48. The transmission optical fiber 46 delivers the chirped optical pulses to the GRIN lens 48 with low or no modal dispersion. Exemplary transmission optical fibers include single mode optical fibers (SMFs), GRIN optical fibers, and serial combinations of GRIN optical fibers and SMFs. The GRIN lens 48 has an optical core with a larger diameter than the optical core of the transmission optical fiber 16. Exemplary GRIN lenses 48 include GRIN rod lenses and GRIN optical fibers. The compound waveguide formed of the transmission optical fiber 46 and the GRIN lens 48 delivers illumination optical pulses to a sample 50. The transmission optical fiber 46 is flexible and thus, enables incorporation of a remote probe (not shown) into the scanning multi-photon imaging system. A movable remote probe is convenient for endoscopic in-vivo imaging applications. The GRIN lens 48 or an auxiliary bulk optical lens (not shown) focuses the illumination optical pulses onto small scan spots 52 in the sample 50.

Illumination portion 40 produces optical pulses that have high peak light intensities and short temporal widths when focused onto scan spots 52 in the sample 50. The high peak intensities provide acceptable illumination to generate molecular multi-photon absorptions, i.e., absorptions of two or more photons, at the high rates desirable for making multi-photon images of the sample 50. Even though the optical pulses have high peak light intensities when focused into the sample 50, the illumination portion 40 maintains peak intensities of the optical pulses therein at low values along the entire illumination delivery pathway. Keeping the peak intensities at low values reduces nonlinear optical effects such as self-phase modulation. These optical effects would temporally broaden optical pulses thereby causing lower peak intensities when the optical pulses are later focused onto scan spots 52 in the sample 50 if the effects were not kept low along substantially the entire length of the illumination delivery pathway.

In the illumination delivery pathway of FIG. 3, the low peak intensity of optical pulses results from an active sculpting of the temporal width of the optical pulses. In general, the peak intensity can be lowered by temporally broadening an optical pulse or by spatially broadening the optical pulse across a larger cross section.

Illumination portion 40 of FIG. 3 uses both methods to lower peak intensities of the optical pulses along the illumination delivery pathway.

Figure 4:
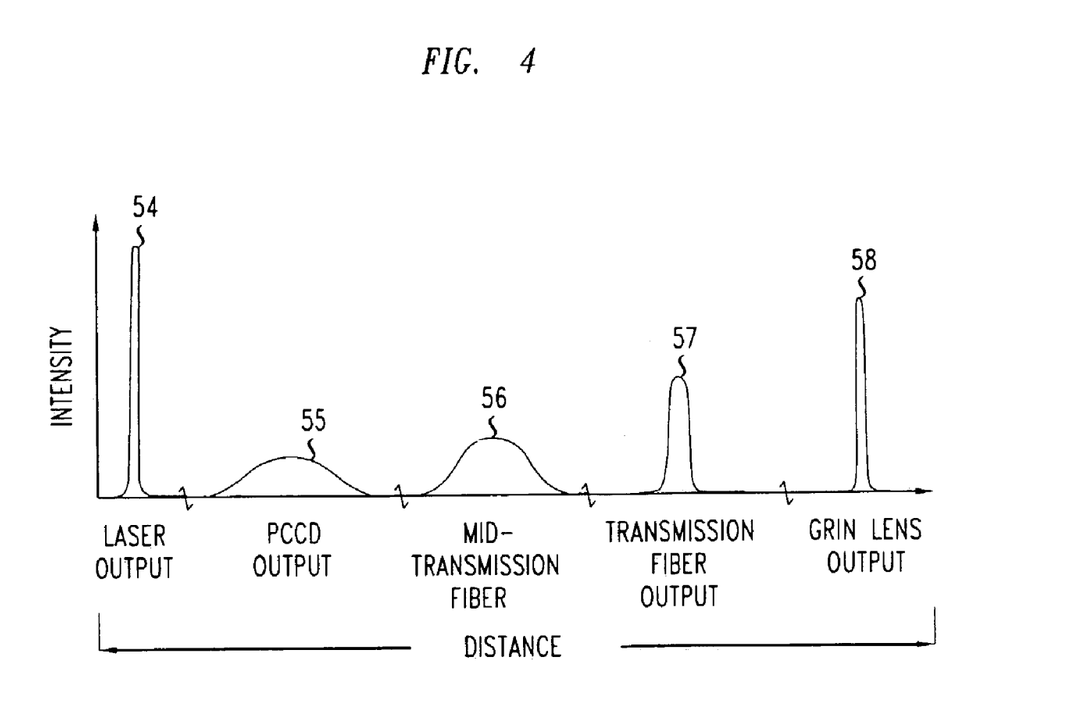
FIG. 4 schematically illustrates the spatial evolution of illumination optical pulses in the illumination portion of the scanning multi-photon imaging system of FIG. 3.

FIG. 4 illustrates the evolution of temporal width and integrated peak intensity, i.e., integrated across the cross section of the beam, for optical pulses propagating in illumination portion 40 of FIG. 3. At the output of pulsed laser 42, the optical pulse 54 has a short temporal width and a high integrated peak intensity. At the output of the PCCD 44, the optical pulse 55 has been chirped so that longer and shorter wavelength components are redistributed toward respective back and front of the optical pulse 55. Chirping produces a broader temporal width than in the optical pulse 54 at the output of the pulsed laser 42. The temporal broadening causes the integrated peak intensity of the chirped optical pulse 55 to be smaller than that of the optical pulse 54 at the output of the pulsed laser 42. The lower peak intensity reduces rates for nonlinear optical interactions in the initial portion of transmission optical fiber 46. At mid-span of the transmission optical fiber 46, chromatic dispersion has produced an optical pulse 56 that is narrower and thus, has a higher peak intensity than the optical pulse 55 at the output of the PCCD 44. The pre-chirping is selected so that optical pulse 57 at the output of the transmission optical fiber 46 while even narrower than the optical pulse 56 at mid-span has still not substantially regained the narrow temporal width of the initial optical pulse 54 at the output of the pulsed laser 42. For that reason, the peak intensity of the optical pulse 56, 57 is low enough to inhibit nonlinear optical distortions thereof along the entire length of the transmission optical fiber 46. Chromatic dispersion continues to cause the received optical pulse to narrow as it propagates through the GRIN lens 48. At the output of the GRIN lens 48, the final optical pulse 58 is substantially narrower than the optical pulse 57 at the output of the transmission optical fiber 46. In exemplary embodiments, the optical pulse 58 at the output of the GRIN lens 48 has substantially the initial temporal width of the optical pulse 54 emitted by the pulsed laser 42.

Figure 5:
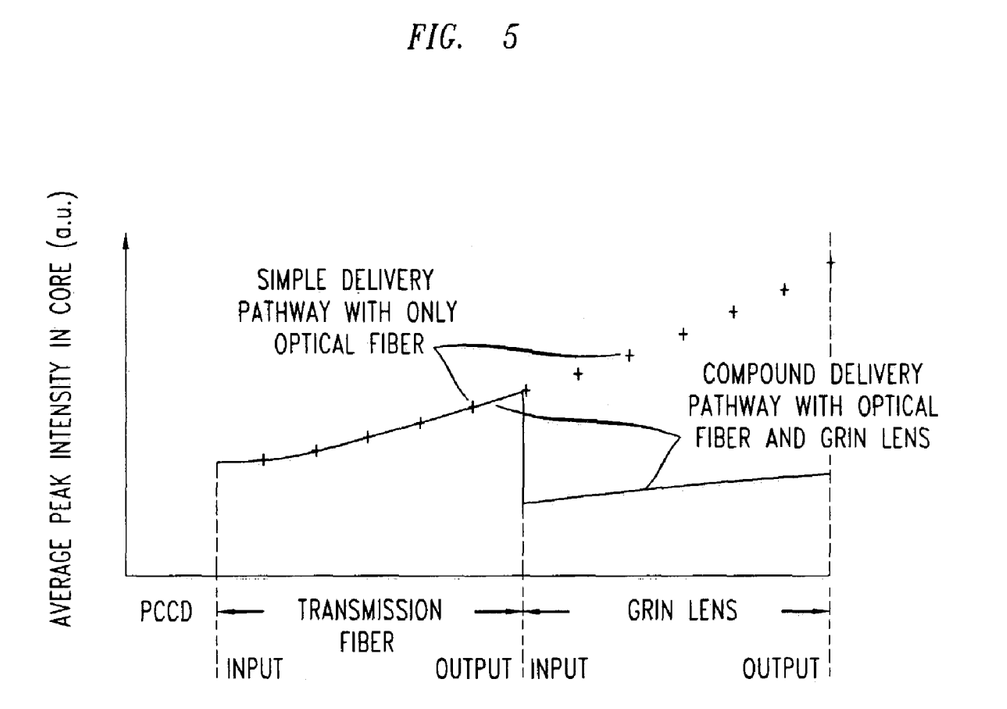
FIG. 5 illustrates the evolution of average light intensities at peaks of optical pulses in the optical waveguide cores of the illumination delivery pathway of FIGS. 3 and 4.

FIG. 5 illustrates how the averaged peak intensity (solid curve) of an optical pulse evolves along a compound illumination delivery pathway that includes transmission optical fiber and GRIN lens 48 of FIG. 3. In FIG. 5, the displayed peak intensities are averaged over the cross section of the optical core in each optical waveguide of the pathway. A crossed curve shows the averaged peak intensity of a comparison simple illumination delivery pathway that includes only the type of fiber of the transmission optical fiber 46. The simple delivery pathway has a length suitable to produce the same final pulse width as the compound delivery pathway, i.e., via the effects of chromatic dispersion.

In both pathways, the averaged peak intensity has a low initial value, because pre-chirping has temporally broadened the optical pulse thereby spreading out the total optical energy in time. As the optical pulse propagates through both pathways, chromatic dispersion narrows the temporal width thereby increasing the averaged peak intensity. In the compound delivery pathway, the averaged peak intensity quickly drops to a lower value in GRIN lens 48 due to the larger cross-sectional area of the optical core therein. As the optical pulse propagates through the GRIN lens 48, chromatic dispersion narrows the temporal width thereby increasing the averaged peak intensity. Nevertheless, the core-averaged peak intensities of optical pulses are lower in the GRIN lens 48 than at corresponding points of the simple delivery pathway.

Applicants note that light intensities of optical pulse peaks that are unaveraged over cross sections of optical cores may actually undergo oscillations along the length of the GRIN lens 48. The oscillations are due to expansion and contraction of the ray bundle in the GRIN lens 48. Nevertheless, except near crossing points of light rays, the maximum light intensities in the GRIN lens 48 are generally lower than in the transmission optical fiber 46. In the GRIN lens 48, light ray crossing points are spaced far apart, i.e., spaced apart by a distance equal to the pitch of the GRIN lens 48. For this reason, on average, the GRIN lens 48 reduces light intensities of peaks of optical pulses with respect to their intensities near the output end of transmission optical fiber 46.

In the compound delivery pathway, GRIN lens 48 has a length sufficient to produce a further substantial narrowing of optical pulses received from transmission optical fiber 46. Herein, substantial narrowing involves reducing the temporal width of an optical pulse enough, i.e., the full width at half maximum, to increase by, at least, 50 percent generic rates at which molecular multi-photon absorptions would be stimulated by such an optical pulse. Since rates for molecular two-photon absorptions are approximately proportional to time-averaged squared intensities, reducing the temporal width of an optical pulse by about a third typically provides substantial narrowing. Reducing the temporal width of an optical pulse by about a third typically increases the pulse's time-averaged square intensity by about a third with respect to the pulse's time-averaged square intensity prior to the narrowing. A narrowing of a third or more produces a substantial increase in generic rates for two-photon absorptions produced by said optical pulses. The GRIN lens 48 preferably narrows the optical pulse by about 50 percent or more. The GRIN lens 48 produces the further narrowing of optical pulses without causing the nonlinear optical distortions that would occur if the temporal narrowing was carried out in transmission optical fiber 46. Non-linear optical distortions are lower in the GRIN lens 48, because peak intensities of the optical pulses are lower on the average.

Referring to FIG. 1, various embodiments of illumination portion 40 fix the relative lengths of transmission optical fiber 46 and GRIN lens 48 so that nonlinear optical effects on optical pulses are low. Lengthening the GRIN lens 48 while simultaneously shortening the transmission optical fiber 46 enables reducing nonlinear optical effects while maintaining the final pulse width, because peak intensities of optical pulses are much lower in the GRIN lens 48 than in the transmission optical fiber 46. Typically, an additional phase, B, which is equal to the integral of $(2\pi/\lambda)(n_2)I$ over the length of the transmission optical fiber 46 and of the GRIN lens 48 satisfies B<1. Here, $\lambda$ and I are the respective wavelength and average peak intensity of the optical pulses in the relevant optical cores, is the cross-sectional area of the optical cores, and $n_2$ is the second order correction to the refractive index, n therein, i.e., $n=n_0+n_2I$. Constraining B to be less than about one suffices to avoid substantial self-phase modulation of optical pulses propagating in the illumination delivery line of FIG. 1. Exemplarily, B<1 and the portion of B due to the integral over the transmission optical fiber 16 is not greater than 0.9B and preferably is not greater than about 0.5B.

Figure 6:
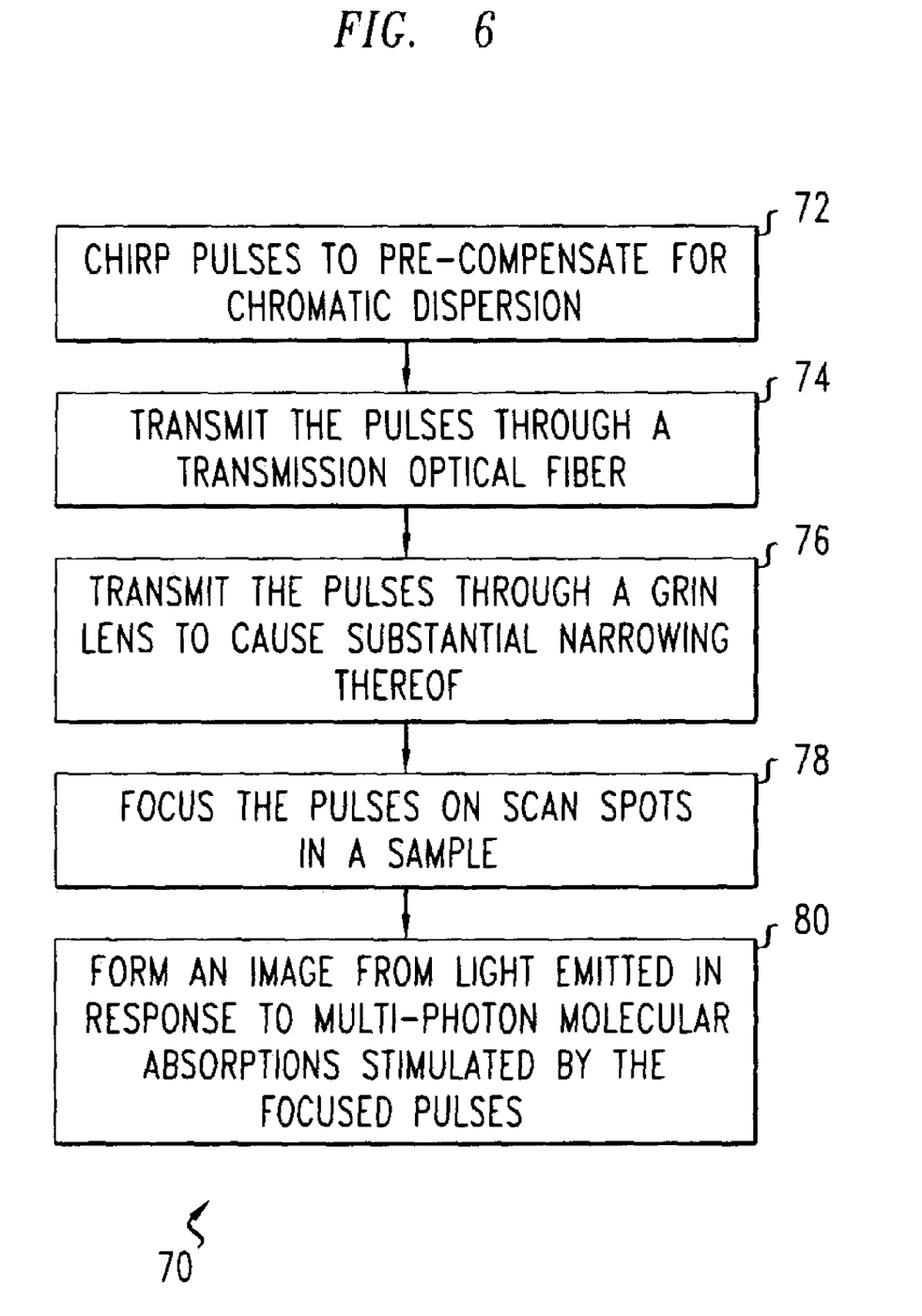
FIG. 6 is a flow chart illustrating a method of operating a scanning multi-photon imaging system.

FIG. 6 illustrates a method 70 for operating a scanning imaging system to produce multi-photon images of a sample. The method 70 includes chirping a series of optical pulses to pre-compensate for chromatic dispersion (step 72). The optical pulses initially have a preselected temporal width and have a wider temporal width after the chirping. The method 70 includes transmitting the chirped optical pulses through a transmission optical fiber with ordinary chromatic dispersion properties (step 74). The chromatic dispersion of the transmission optical fiber narrows the temporal widths of the chirped optical pulses as they propagate there through. The transmission optical fiber may, e.g., provide a flexible connection to a remote probe. The method 70 includes transmitting the optical pulses outputted from the transmission optical fiber through a GRIN lens (step 76). The GRIN lens has ordinary chromatic dispersion properties that produce a further substantial temporal narrowing of the pre-chirped optical pulses transmitted through the transmission fiber. The method 70 includes focusing the further narrowed optical pulses from the GRIN lens onto scan spots in the sample (step 78). Finally, the method 70 includes forming an image of the sample from light emitted in response to molecular multi-photon absorptions in the sample (step 80). The light is emitted in response to the focusing of the further narrowed optical pulses onto the scan spots of the sample.

Figure 7:
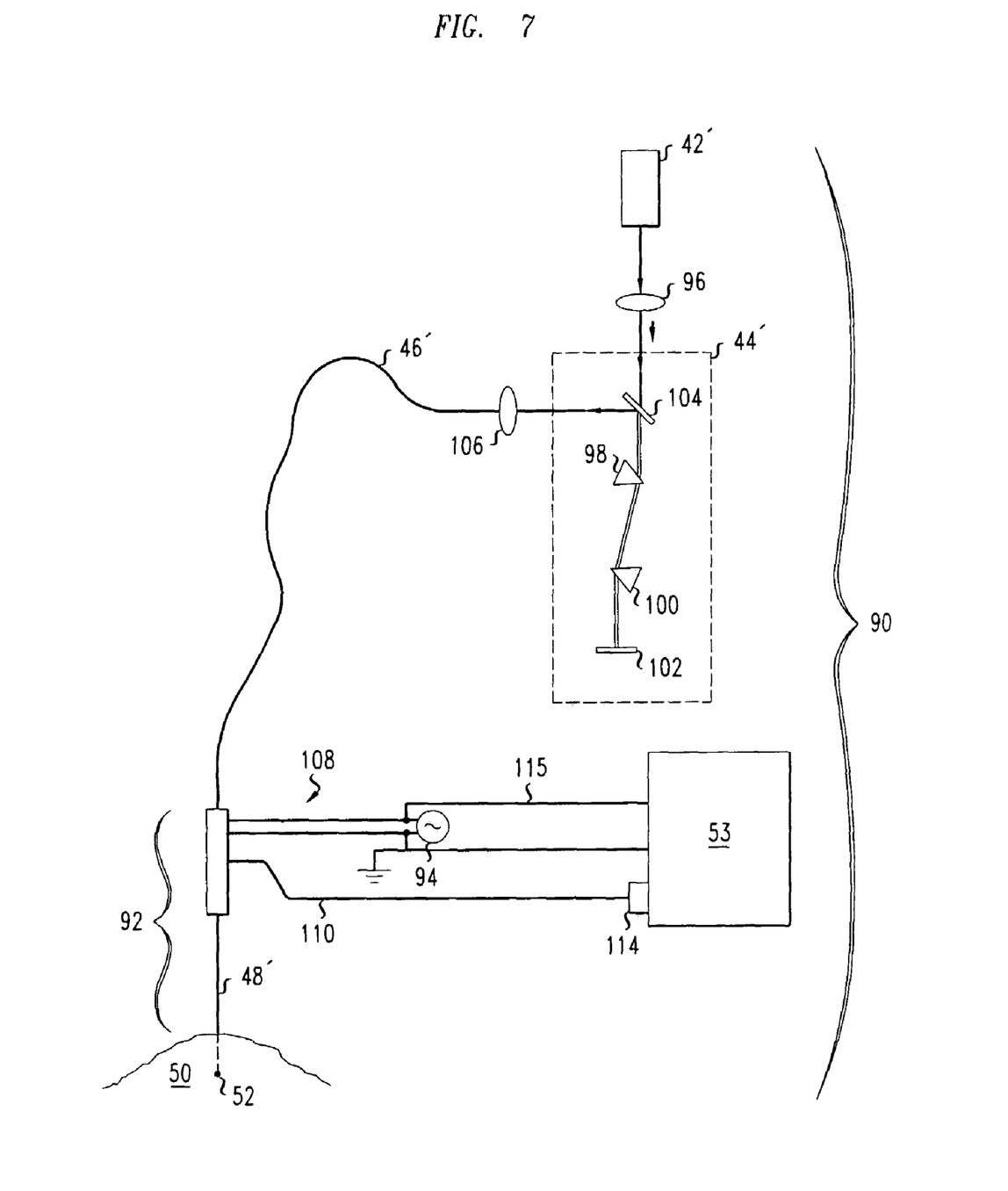
FIG. 7 shows a specific scanning multi-photon imaging system that has an illumination portion described by FIGS. 3–5.

FIG. 7 shows a specific embodiment of a scanning multi-photon imagining system 90. The imaging system 90 includes a pulsed laser 42', a pre-compensator for chromatic dispersion (PCCD) 44', a single-mode transmission optical fiber SMTF 46', a GRIN lens 48', a processor 53, a mobile endoscopic probe 92, and an AC voltage driver 94. The imaging system 90 is capable of producing images of structures located inside a living biological organ or tissue mass.

In the imaging system 90, the pulsed laser 42' provides ultra-fast optical pulses, e.g., with widths of less than a pico-second and preferably less than about 400 femto seconds. The pulses that have high peak intensities and visible or near infra-red wavelengths. An exemplary pulsed laser 42' is the Tsunami, mode-locked titanium-sapphire laser of Spectra-Physics Lasers Inc., 1335 Terra Bella Ave., Mountain View, Calif. 94043. The Tsunami laser produces optical pulses having intensities of about $4\times10^{10}$ to about $40\times10^{10}$ photons, temporal widths of about $8\times10^{-14}$ seconds to about $10^{-13}$ seconds, and wavelengths in the range of about 82 nanometers (nm) to about 850 nm.

In the imaging system 90, the PCCD 44' receives optical pulses from pulsed laser 42' via a collimating lens 96 and chirps the received optical pulses to pre-compensate for the effects of chromatic dispersion in other parts of the illumination delivery pathway. The PCCD 44' includes a pair of Brewster angle prisms 98, 100, a high quality reflector 102, and an optical pick off device 104. The PCCD 44' functions as a double-pass device, in which an optical pulse passes through each prism 98, 100 twice such that the optical pulse is appropriately on the return path. The pick-off device 104 is either a birefringent slab or partially reflecting mirror that deflects a portion of the chirped optical pulse to the remainder of the illumination delivery pathway.

In the imaging system 90, the lens 106 focuses chirped optical pulses from the PCCD 44' into a first end of SMTF 46'. The SMTF 46' transports the chirped optical pulses from the PCCD 44' to remote endoscopic probe 92 without broaden effects associated with the modal dispersion inherent in multi-modal optical fibers. The flexibility of the SMTF 46' enables an operator to position the remote endoscopic probe 92 in convenient positions for in vivo medical diagnostic imaging.

Figure 8:
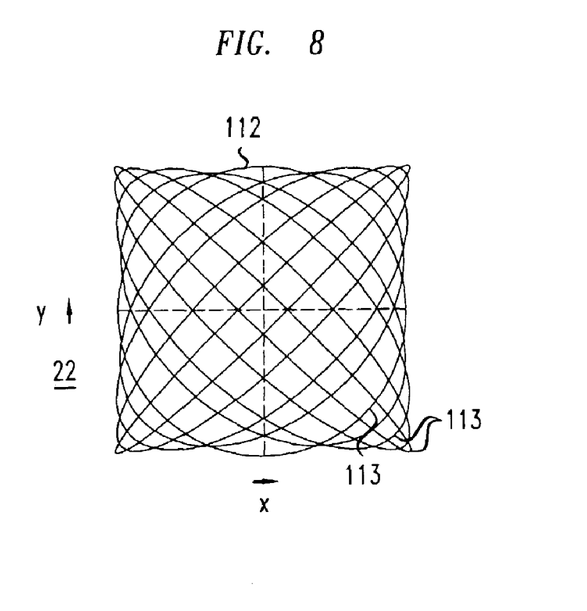
FIG. 8 shows the Lissajous pattern traced out by the scan light in one embodiment of the scanning multi-photon imaging system shown in FIG. 7.

In the imaging system 90, the remote endoscopic probe 92 includes GRIN lens 48', a mechanical scanner (not shown), power lines 108, and a collection optical fiber 110. The GRIN lens 48' delivers optical pulses received from SMTF 46' to sample 50 and collects light emitted by spots 52 of the sample 50 that have been illuminated by the optical pulses. The GRIN lens 48' has a wider optical core than the SMTF 46', e.g., two or more times as wide. Typically, the GRIN lens 48' has a core diameter of about 80–125 microns or more as compared to the core diameter of about 5–15 microns for the SMTF 46'. The GRIN lens 48' substantially narrows optical pulses received from the SMTF 46', e.g., the pulses may be narrowed by 30 percent or more in the GRIN lens 48'. The mechanical scanner causes optical pulses from the SMTF 46' to traverse a 2-dimensional self-crossing scan pattern in response to an AC driving voltage applied via the power lines 108. An exemplary scan pattern is the Lissajous pattern 112 shown in FIG. 8. The collection optical fiber 110 delivers to light intensity detector 114 light that the GRIN lens 48' collects from the sample 50. Exemplary light intensity detectors 114 include photo-multiplier tubes.

In the imaging system 90, the processor 53 produces scanned multi-photon images of sample 50 by processing measured light intensities from light intensity detector 114 and voltages outputted by AC voltage driver 94, i.e., voltages measured via line 115. The measured voltages indicate positions of scan spots along a Lissajous pattern when the end of transmission optical fiber 46' is performing a steady state scanning motion. Circuits and methods for extracting scan position data from AC driving voltages are well-known in the art and, e.g., are described in U.S. patent application Ser. No. No. 09/971,856, ('856 application) filed Oct. 05, 2001 by W. Denk et al, which is incorporated herein by reference in its entirety.

Figure 9:
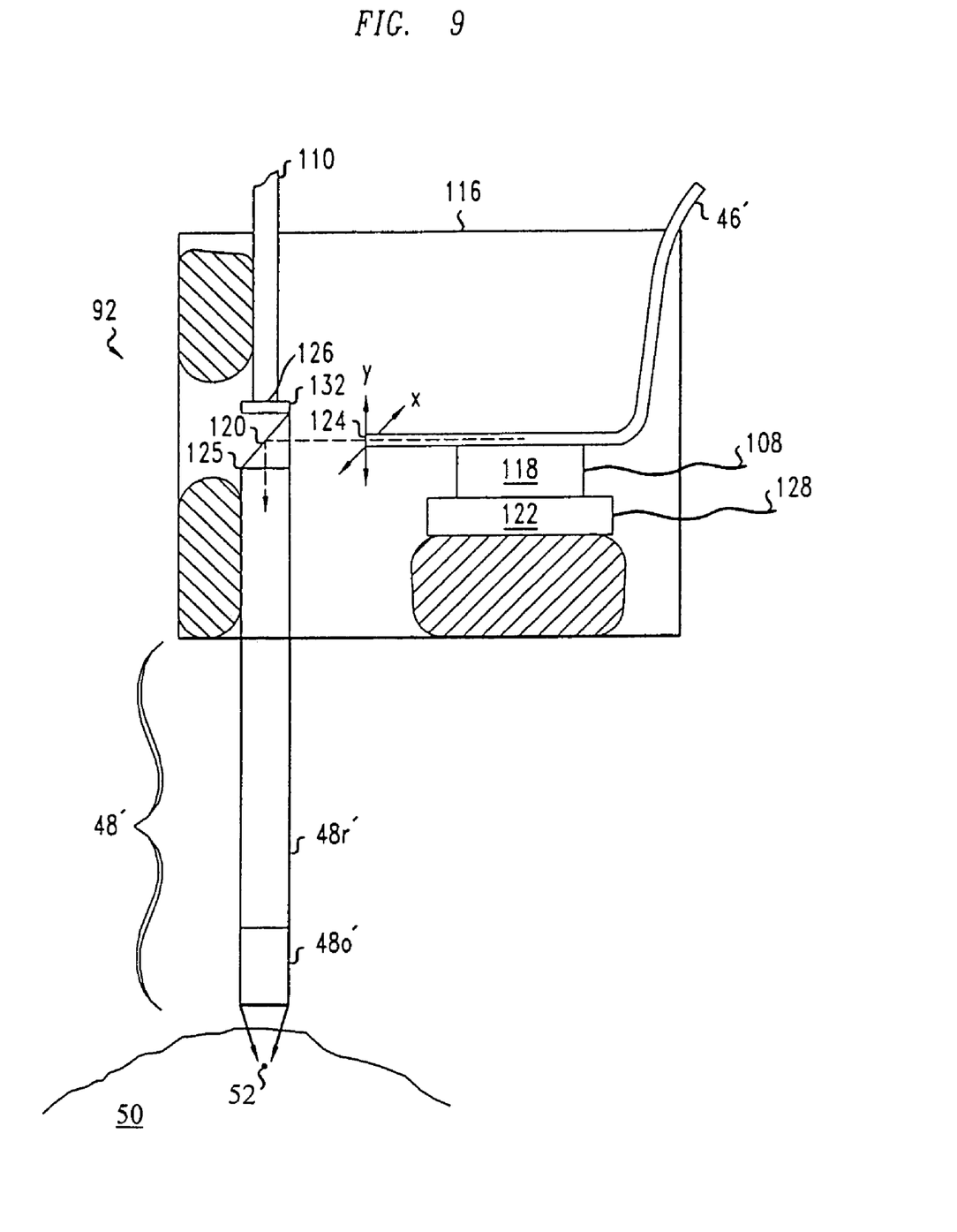
FIG. 9 shows a remote endoscopic probe used in the scanning multi-photon imaging system of FIG. 7.

Referring to FIG. 9, the remote endoscopic probe 92 includes a rigid cylindrical housing 116. The housing 116 holds a mechanical oscillator 118, a 45° angle prism 120, a focal length controller 122, a filter 132, and ends 124–126 of SMTF 46', GRIN lens 48', and collection optical fiber 110. The focal length controller 122 and waveguide ends 125–126 are immovably fixed to the rigid housing 116. A portion of the SMTF 46' is rigidly fixed to the mechanical oscillator 118, which is in turn rigidly fixed to the focal length controller 120. The end 124 of the SMTF 46' is able to move with respect to the 45° angle prism 120.

The mechanical oscillator 118 is a piezoelectric bimorph or multi-layered structure that bends in response to an AC drive signal that lines 108 apply between central and outer layers thereof. The bending generates a transverse scan motion by free end 124 of the SMTF 46'. An AC voltage signal with two frequency components $f_x$ and $f_y$ produces a steady-state scan motion whose transverse X and Y coordinates depend on time, t, as:

$$X(t)=A_x \cos(2\pi f_x t+\phi_x) \text{ and } Y(t)=A_y \cos(2\pi f_y t+\phi_y).$$

Here, $\phi_x$ and $\phi_y$ are phase lags of the scan motion of the free end 124 behind the driving AC voltage signal. One of skill in the art would know how to measure such phase lags from the frequencies and amplitudes of the AC driving voltages and would be able to construct apparatus for determining the X(t) and Y(t) scan coordinates dynamically. Methods and circuits for determining the two scan coordinates from the AC driving voltages are also described in the above-referenced '856 application.

Figure 10A:
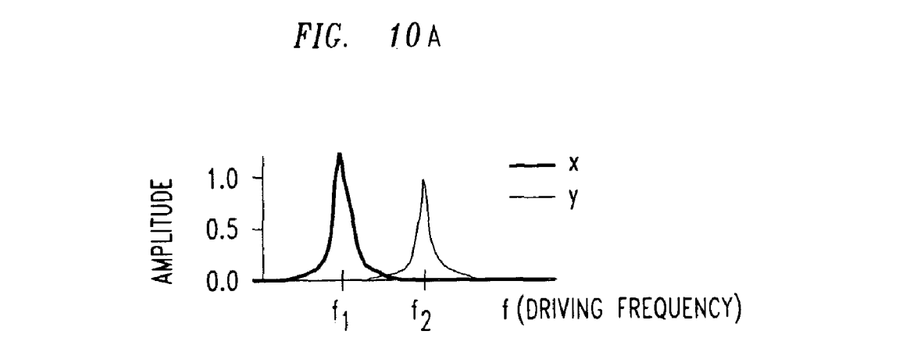
FIGS. 10A and 10B show the respective amplitude and phase of X motion and Y motion of a radially asymmetric fiber end driven at a frequency f.
Figure 10B:
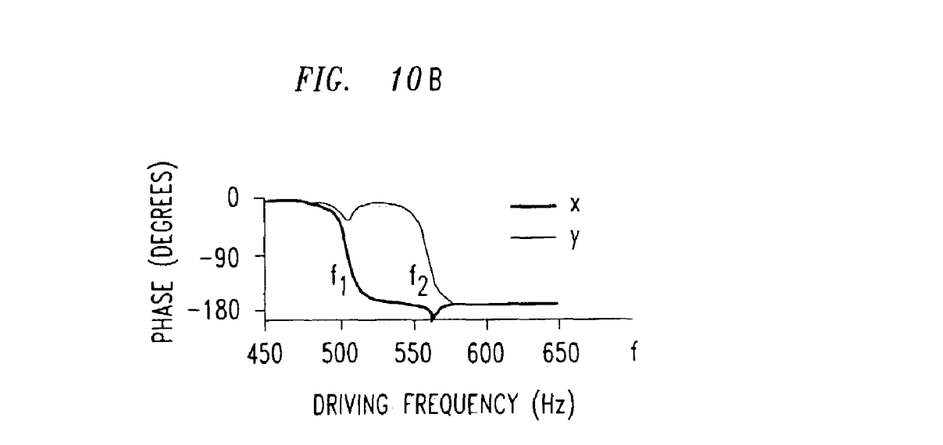
Figure 11A:
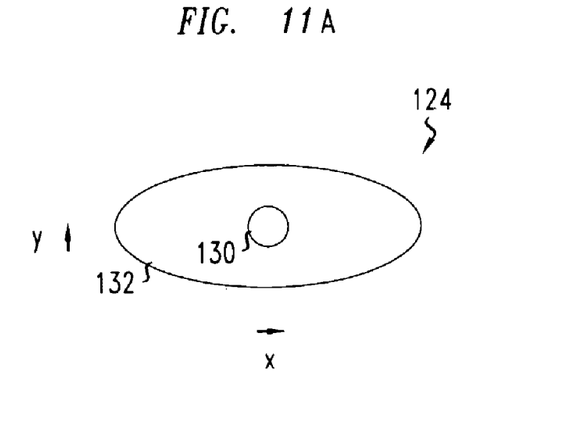
FIGS. 11A–11B are cross-sectional views of end portions of optical fibers that trace out self-crossing scan patterns when simultaneously driven at two frequencies.
Figure 11B:
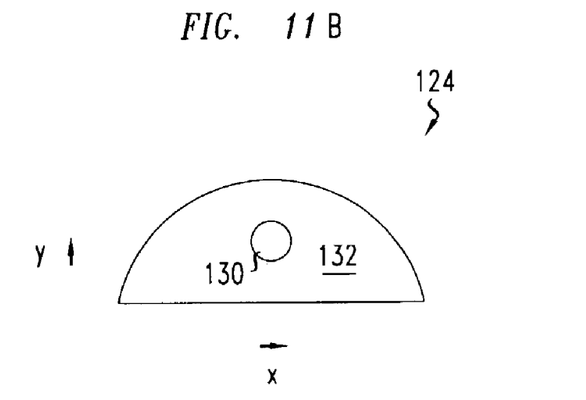
Figure 11C:
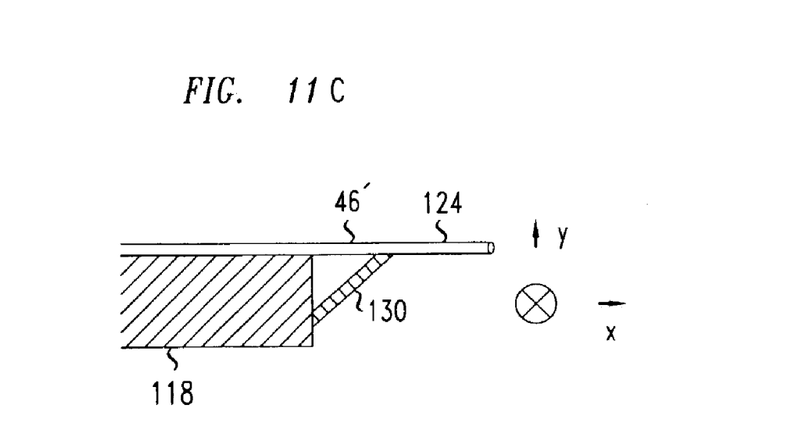
FIG. 11C is a side view of an end portion of an optical fiber that has been stiffened to trace out a self-crossing scan pattern when simultaneously driven at two frequencies.

The driving frequencies $f_x$ and $f_y$ produce near resonant responses in the X and Y coordinates of fiber end 124. FIGS. 10A and 10B show amplitude and phase of the steady state oscillation of one fiber end 124 that has X and Y resonances at frequencies $f_1$ and $f_2$, respectively. For a scan pattern that forms a self-crossing Lissajous figure, e.g., the pattern 112 of FIG. 8, free fiber end 124 should have different bending constants in the X direction and the Y direction. In the free fiber end 124, which includes optical core 130 and optical cladding 132, some optical fibers have different X- and Y-direction bending constants, because the cladding 132 has an either an oval cross section or a D-shaped cross section as shown in FIGS. 11A and 11B. In the free fiber end 124, some other optical fibers have different X- and Y-direction bending constants, because the free end 124 has been stiffened in the Y-direction with a semi-rigid strut 130. The semi-rigid strut 130 connects to an end face of mechanical oscillator 118 as shown in FIG. 11C. Methods for calibrating and producing such 2-dimensional self-crossing scan patterns are also described in the above-incorporated '856 application.

The 45° angle prism 120 is a direct optical coupler. A back surface of the prism 120 reflects light received from scanning end 124 of SMTF 46' into GRIN lens 48'. The prism 120 also directs collected light from GRIN lens 48' into collection optical fiber 110.

The focal length controller 122 is a piezoelectric structure that regulates the lateral separation between fiber end 124 and 45° angle prism 110. The focal length controller 122 is responsive to a voltage on line 128. The lateral separation the fiber end 124 and the 45° angle prism fix the depth of focused spot 52 formed by the scan beam in sample 50.

The GRIN lens 48' is either a rod or fiber lens. The GRIN lens 48' delivers illumination optical pulses to sample 50 and collects light emitted in response to molecular multi-photon absorptions caused by the optical pulses. The GRIN lens 48' or an attached ordinary lens (not shown) focus the optical pulses onto small scan spots 52 in the sample 50. GRIN lens 48' has a length of between ½ to ¼ modulo an integer times the GRIN lens' pitch. The GRIN lens 48' is also long enough to substantially narrow temporal widths of optical pulses received from SMTF 46' thereby increasing peak light intensities in the sample 50 as already described with respect to FIGS. 3–5. The GRIN lens 48' is a compound lens that includes a short pitch objective GRIN lens 48o' and a relatively longer pitch relay GRIN lens 48r'. Exemplary objective and relay GRIN lenses have lengths equal to about ¼ and ¾ modulo ½ integers times their respective pitches. Configurations for such compound GRIN lenses 48' are described in U.S. patent application Ser. No. 10/082,870 filed Feb. 25, 2002 by Mark J. Schnitzer, which is incorporated herein by reference in its entirety. In other embodiments of scanning multi-photon imaging system 90, GRIN lens 48' is a simple GRIN lens.

The collection optical fiber 110 is a multi-mode optical fiber that transports collected multi-photon light, which is received from GRIN lens 48', to light detector 114. Optical filter 132 removes back-reflected light with the wavelength of the illumination optical pulses from entering the collection optical fiber 110.

Referring to FIG. 7, the processor 53 compensates for spatial variations in scanning speed and scan spot density in producing a scanning image of sample 50. For example, scanning speeds are lower near turning points 113 of Lissajous pattern 112 of FIG. 8. Producing a scanning image of the sample 50 includes multiplying light intensities measured by light detector 114 by a weight factor that compensates for variations in the scanning speed. Methods and devices for compensating for variations in the scanning speed and scanning spot densities are also described in the '856 application.

From the disclosure, drawings, and claims, other embodiments of the invention will be apparent to those skilled in the art.

What is claimed is:

1. An imaging system, comprising:
   a pulsed laser;
   a pre-compensator configured to receive optical pulses produced by the pulsed laser and to chirp said optical pulses to pre-compensate for chromatic dispersion;
   a transmission optical fiber configured to receive and transport the chirped optical pulses from the pre-compensator;
   a GRIN lens configured to receive the optical pulses transported by the transmission optical fiber; and
   wherein the GRIN lens has a wider optical core than the transmission optical fiber and the GRIN lens is configured to substantially temporally narrow the optical pulses received from the transmission optical fiber.

2. The system of claim 1, wherein the transmission optical fiber is a single-mode optical fiber.

3. The system of claim 1, wherein the GRIN lens is configured to temporally narrow the optical pulses received from the transmission optical fiber by about 50 percent or more.

4. The system of claim 3, wherein the transmission optical fiber is a single-mode optical fiber.

5. The system of claim 4, wherein the GRIN lens is configured to temporally narrow the optical pulses received from the transmission optical fiber by about 30 percent or more.

6. The system of claim 1, wherein the pulsed laser is configured to produce optical pulses with temporal widths of less than about 400 femto seconds.

7. The system of claim 1, further comprising:
   a light detector configured to detect an intensity of light collected from a sample by the GRIN lens in response to the sample being illuminated by optical pulses delivered by the GRIN lens.

8. The system of claim 7, further comprising a mechanical oscillator configured to cause the optical pulses delivered by the GRIN lens to scan over a self-crossing Lissajous pattern in the sample.

9. The system of claim 8, further comprising a processor configured to produce an image of the sample from data indicative of positions illuminated by the delivered optical pulses and corresponding light intensities detected by the light detector.

10. The system of claim 1, further comprising another optical lens coupled to an end of the GRIN lens located opposite to an end of the GRIN lens that receives optical pulses from the transmission optical fiber.

11. A method for operating an imaging system, comprising:
    chirping optical pulses;
    transmitting the chirped optical pulses through a transmission optical fiber wherein chromatic dispersion narrows the chirped optical pulses;
    transmitting through a GRIN lens the optical pulses transmitted through the transmission optical fiber; and
    wherein the transmitting through a GRIN lens causes further substantial temporal narrowing of the optical pulses transmitted through the transmission optical fiber.

12. The method of claim 11, wherein the transmitting the chirped optical pulses comprises inserting the chirped optical pulses in a single mode optical fiber.

13. The method of claim 11, further comprising:
    focusing the optical pulses transmitted through the GRIN lens onto spots of a self-crossing scanning pattern in a sample.

14. The method of claim 11, wherein the focusing further comprises driving a mechanical oscillator with a voltage that includes two driving frequencies.

15. The method of claim 13, further comprising:
    forming an image of the sample from light emitted by the sample in response to molecular multi-photon absorptions caused by the focusing.

16. The method of claim 13, further comprising:
    forming an image of the sample from light emitted by the sample in response to molecular two-photon absorptions caused by the focusing.

* * * * *